(12) United States Patent
Bates

(10) Patent No.: US 6,786,098 B2
(45) Date of Patent: Sep. 7, 2004

(54) MATERIAL ANALYSIS

(75) Inventor: Daniel Bates, Coventry (GB)

(73) Assignee: Airbus UK Limited, Bristol (GB)

( * ) Notice: Subject to any disclaimer, the term of this patent is extended or adjusted under 35 U.S.C. 154(b) by 0 days.

(21) Appl. No.: 10/181,263

(22) PCT Filed: Jan. 19, 2001

(86) PCT No.: PCT/GB01/00223

§ 371 (c)(1),
(2), (4) Date: Jul. 25, 2002

(87) PCT Pub. No.: WO01/53821

PCT Pub. Date: Jul. 26, 2001

(65) Prior Publication Data

US 2003/0010124 A1 Jan. 16, 2003

(30) Foreign Application Priority Data

Jan. 20, 2000 (GB) .............................................. 0001181

(51) Int. Cl.⁷ ............................. G01N 29/04; G01J 5/02
(52) U.S. Cl. ....................... 73/606; 73/602; 250/341.6; 250/334
(58) Field of Search ................ 73/606, 602; 250/341.6, 250/334; 374/4, 5, 47, 57, 45, 121, 117

(56) References Cited

U.S. PATENT DOCUMENTS

| 4,607,341 A | | 8/1986 | Monchalin | |
|---|---|---|---|---|
| 4,683,750 A | * | 8/1987 | Kino et al. | 73/606 |
| 5,201,841 A | * | 4/1993 | Lebeau et al. | 374/5 |
| 5,287,183 A | * | 2/1994 | Thomas et al. | 348/571 |
| 5,381,695 A | * | 1/1995 | Payne et al. | 73/643 |
| 5,386,727 A | | 2/1995 | Searle | |
| 5,631,465 A | * | 5/1997 | Shepard | 250/330 |
| 5,974,881 A | | 11/1999 | Donskoy et al. | |
| 6,236,049 B1 | * | 5/2001 | Thomas et al. | 250/341.6 |

FOREIGN PATENT DOCUMENTS

| EP | 0370801 A1 | 5/1990 |
|---|---|---|
| EP | 0535881 A1 | 4/1993 |
| GB | 785 775 A | 7/1955 |
| GB | 2 194 062 A | 2/1988 |
| SU | 1 075 143 | 2/1984 |
| SU | 1 200 675 A | 7/1990 |

* cited by examiner

Primary Examiner—Hezron Williams
Assistant Examiner—Jacques M. Saint-Surin
(74) Attorney, Agent, or Firm—Nixon & Vanderhye P.C.

(57) ABSTRACT

Material analysis apparatus and method, particularly of use in detecting barely visible impact damage but also of use to detect other material characteristics. The apparatus includes a function generator which provides a sinusoidal signal to an ultrasonic amplifier as well as to a PC. The PC is connected to an infrared camera. The sinusoidal signal is fed into the amplifier and causes two probes attached to the sample of material to emit ultrasonic energy at the modulated frequency. Ultrasonic energy from the two probes then enters the sample by means of mechanical coupling and an image of the resulting thermal radiation is captured by the infrared camera and transferred to the PC for further processing and analysis.

17 Claims, 5 Drawing Sheets

# MATERIAL ANALYSIS

This application is the US national phase of international application PCT/GB01/00223 filed Jan. 19, 2001, which designated the US.

BACKGROUND OF THE INVENTION

1. Field of the Invention

The present invention relates to material analysis.

2. Discussion of Prior Art

Known methods of material analysis include using an intensity modulated ultrasonic source to measure material properties. In such prior art systems, a single ultrasonic probe operating at a single frequency is aimed towards a sample of a material. The resulting vibrations through the sample are measured in order to obtain data about the sample.

The known ultrasonic material analysis apparatus uses only one ultrasonic transducer operating at a single frequency with an amplitude modulated by a second frequency and using intensity detectors to obtain a reading of ultrasonic absorption. However, this approach results in standing waves being set up in the sample under inspection and generating hot spots. These hot spots are indistinguishable from damaged areas and so often result in misidentification of damage within the sample. This approach also has the disadvantage that readings can only be obtained for the overall probed area and does not allow finer analysis of sub-regions within the area.

It is also known to use lock-in thermography techniques to analyse materials. This involves aiming a halogen lamp at a sample and modulating the intensity sinusoidally with a known frequency. An infra-red camera then captures a thermal image of a surface of the sample at the modulated frequency.

Whilst these prior art techniques can be useful for several types of material analysis, they are limited in usefulness for detecting barely visible impact damage (BVID) which exhibit areas of shattered material.

SUMMARY OF THE INVENTION

An object of the present invention is to provide a material analysis technique which can produce improved results in detecting BVID and other material characteristics.

According to a first aspect of the present invention there is provided apparatus for material analysis including:

means for directing vibrational energy into a material sample in sufficient quantity to generate heat in the sample; and means for capturing a thermal image of the sample.

Preferably, the thermal imaging is adapted to detect heat emitted from a damage site in the sample. The means for directing vibrational energy into the sample preferably generates vibrations in the frequency range 10 Hz to 1 MHz, and more preferably in the ultrasonic frequency range.

Preferably, the ultrasonic energy emitting means includes two ultrasonic probes for being attached to the sample. Preferably, the two probes in use emit sonic energy at different respective frequencies. Preferably, the apparatus includes means for modulating the intensity of the sonic energy emitted by each of the probes.

In a preferred embodiment, one of the two probes operates at a frequency of approximately 35 kHz and the other operates at a frequency of approximately 40 kHz. Preferably, the modulating means modulates the intensities of the two probes $\rho/2$ out of phase with each other. The modulation frequency may be between 0.01 and 2.0 Hz.

The means for capturing the thermal image may be configured to sample at an integer multiple of the modulation frequency, preferably at approximately twice the modulation frequency.

The means for capturing the thermal image preferably includes an infra-red camera.

According to a second aspect of the present invention there is provided a method of material analysis including steps of:

directing vibrational energy into a material sample; and capturing a thermal image of the sample.

Preferably, the step of directing vibrational energy into the sample includes attaching two probes to the sample, the probes being configured to operate at two different respective frequencies. Preferably, the intensities of the two probes are modulated out of phase with each other.

Whilst the invention has been described above it extends to any inventive combination of features set out above or in the following description.

BRIEF DESCRIPTION OF EMBODIMENTS

The invention may be performed in various ways, and various embodiments thereof will now be described in detail, reference being made to the accompanying drawings in which.

Figure 9:
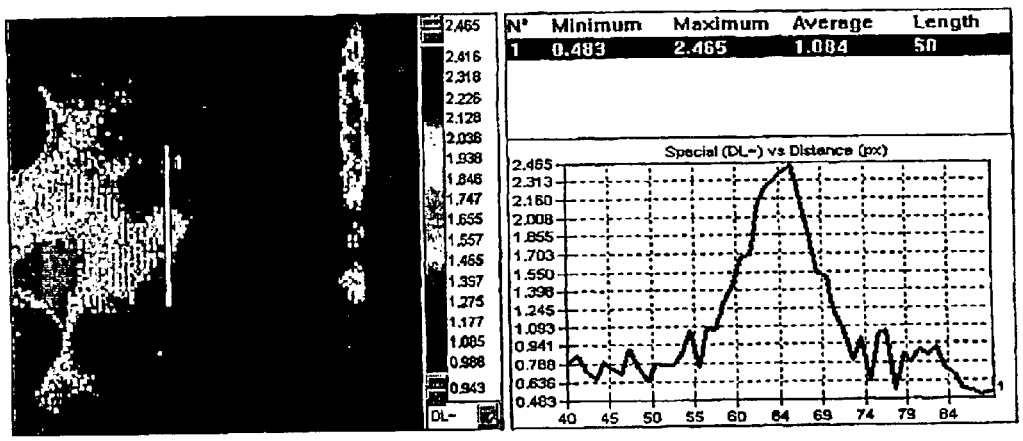
Figure 10:
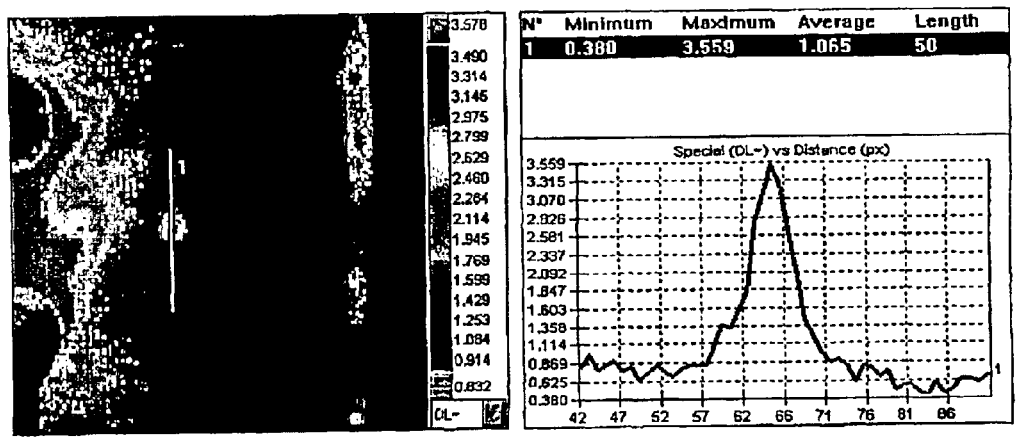
Figure 11:
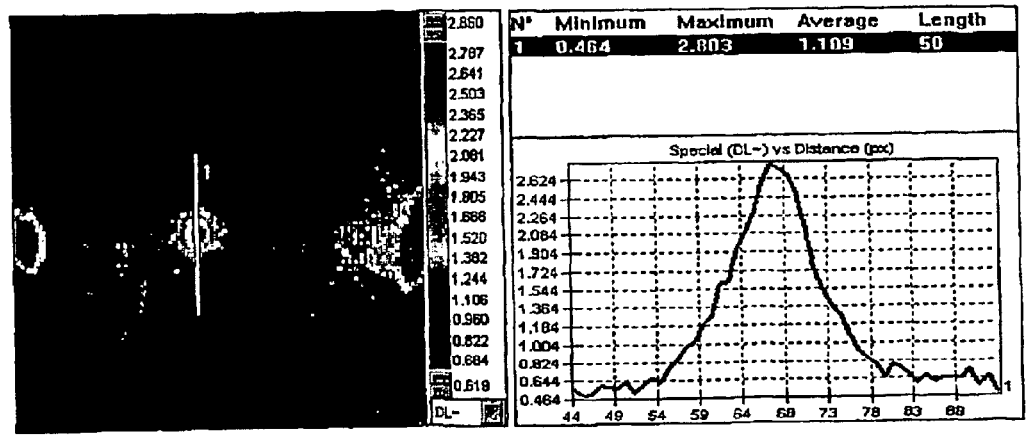
Figure 12:
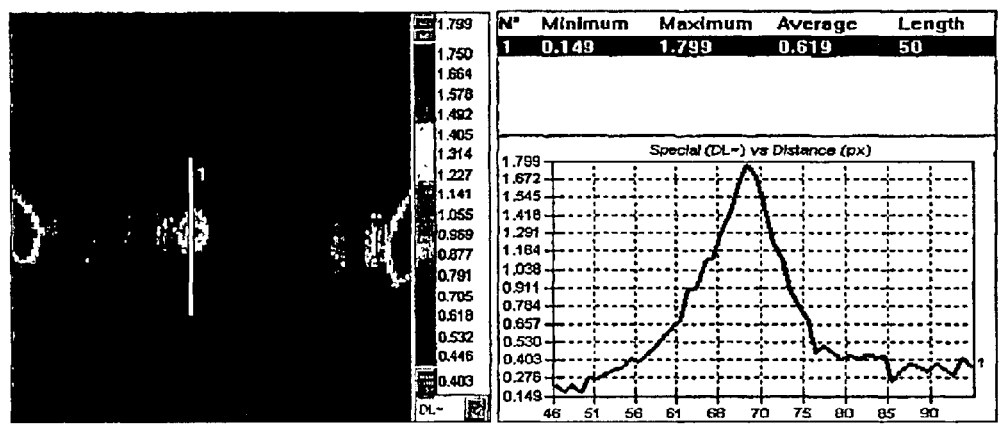
Figure 13:
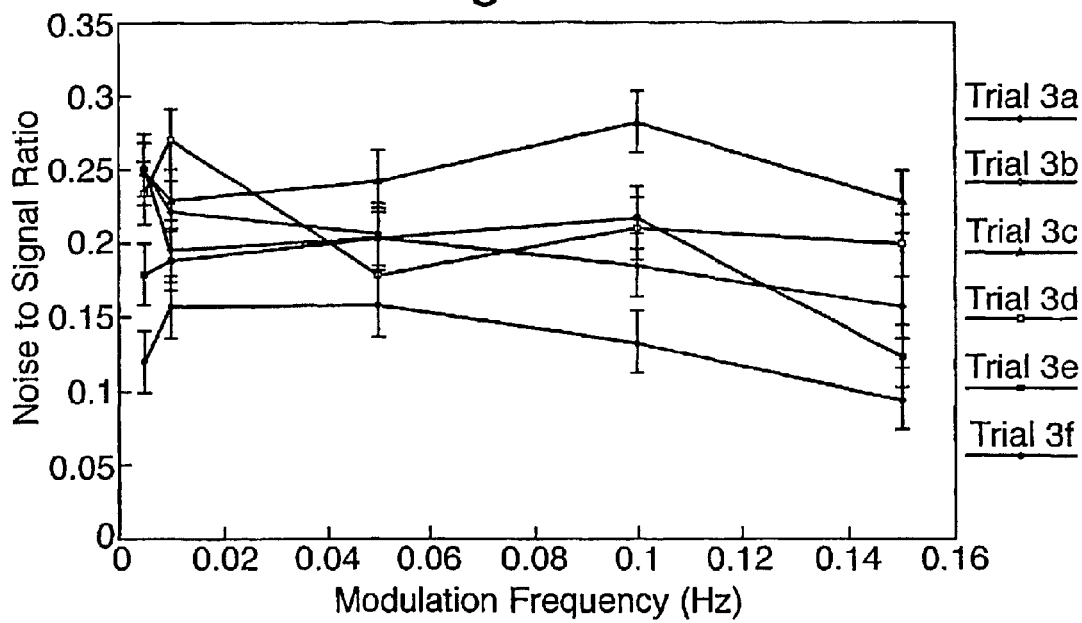

FIG. 9 shows an amplitude image for vertically oriented 35 kHz and 40 kHz sonotrodes using 0.15 Hz modulation frequency in phase;

FIG. 10 shows an amplitude image for vertically oriented 35 kHz and 40 kHz sonotrodes using 0.05 Hz modulation frequency out of phase;

FIG. 11 shows an amplitude image for horizontally oriented 35 kHz and 40 kHz sonotrodes using 0.15 Hz modulation frequency in phase;

FIG. 12 shows an amplitude image for horizontally oriented 35 kHz and 40 kHz sonotrodes using 0.15 Hz modulation frequency out of phase;

FIG. 13 shows noise to signal ratio for all ultrasonic lock-in trials against frequency.

DETAILED DISCUSSION OF EMBODIMENTS

Figure 1:
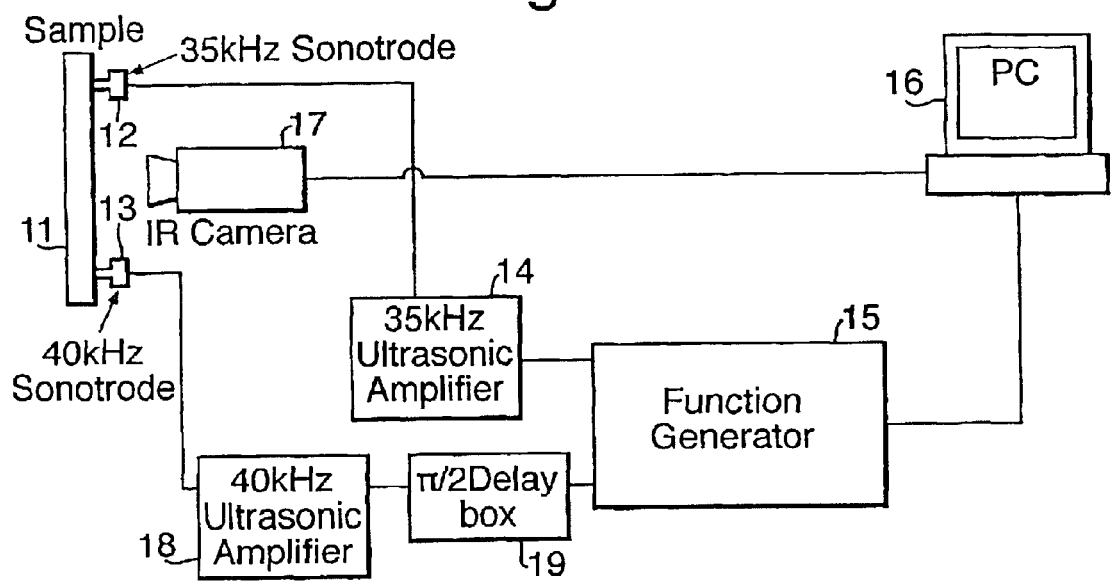
FIG. 1 is a schematic view of a preferred embodiment of the present invention.

In FIG. 1, a sample 11 of a material to be analysed has two ultrasonic probes (sonotrodes/ultrasonic transducers) 12 and 13 attached to it. The two probes are each connected to an ultrasonic amplifier 14, 18. The amplifiers 14, 18 are connected to a function generator 15 which provides a sinusoidal signal to the amplifiers as well as to a personal computer (PC) 16. Amplifier 18 receives its signal from the function generator 15 via a delay box 19 which acts to render the respective ultrasonic energy signals from probes 12, 13 $\rho/2$ out of phase with each other. The PC 16 is also connected to an infra-red camera 17, which has a lens pointing towards a surface of the sample 11 and is capable of capturing thermal images.

The sinusoidal signal generated by component 15 is fed into the amplifiers 14 and 18 and causes the two probes 12 and 13 to emit ultrasonic energy at the modulated frequency. Ultrasonic energy from the two probes then enters the sample 11 by means of mechanical coupling and causes the whole component to be set into small amplitude oscillation through material lattice vibrations (phonons). Areas of impact damage, including BVID, dissipate the ultrasonic energy in the form of thermal energy at a higher rate than non-damaged material. The dissipated ultrasonic energy is then transported to the surface of the sample and emitted in the form of thermal radiation. An image of this thermal radiation can then be captured by the infra-red camera 17 and transferred to the PC 16 for further processing and analysis.

The use of the two ultrasonic probes 12 and 13 operating at different respective frequencies means that problems resulting from standing wave generation are minimised or eliminated. In this example, the operating frequency of the first probe 12 is approximately 35 kHz and the frequency of the second probe 13 is approximately 40 kHz. The intensities of both of the probes are modulated $\rho/2$ out of phase by the frequency generated by the function generator 15. The infrared camera 17 is configured to sample at twice this modulation frequency to perform the thermal image capture. The modulation frequency can be varied, typically in a range between 0.01 and 2.0 Hz.

A co-pending patent application of the inventor demonstrates effectiveness at detecting BVID in small coupons with the ability to detect a small defect with ease. However, resonance of the coupons was observed with an amplitude of up to 20% of the maximum peak of that showing for the BVID site, which could potentially confuse a user. In addition, questions about the attenuation of the ultrasound over the large areas necessary to inspect items such as an aircraft wing J-nose were raised, which could render the technique unusable for the in-service environment.

Figure 2:
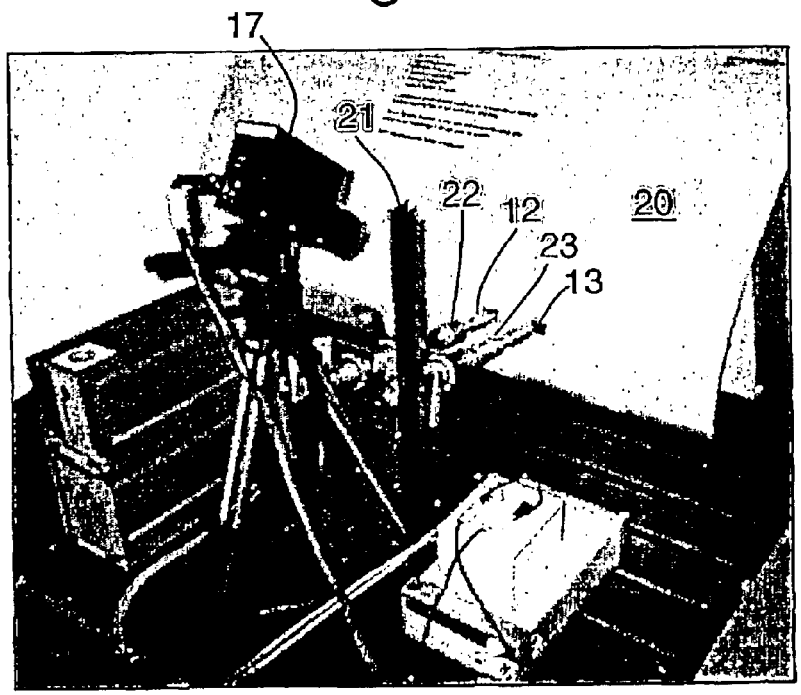
FIG. 2 is a pictorial representation of equipment to implement the modified amplitude modulated lock-in ultrasonic TNDT technique.

The apparatus of the invention was devised to minimise the problem of component resonance and is illustrated schematically in FIG. 1 and pictorially on the J-nose 20 in FIG. 2. It could also contribute to overcoming the problem of signal attenuation by spreading the input ultrasound over a larger area by using two ultrasonic sonotrodes.

FIG. 2 illustrates the transducer heads and the mechanical coupling of the transducers to an aircraft wing J-nose demonstrator by using a clamping unit 21 and spring loaded mechanisms 22, 23 to maintain a constant pressure. A booster was added between the sonotrode and transducer in a reverse manner so that the amplitude of the ultrasonic wave was halved to reduce the heating effect directly under the sonotrode head. PTFE plumbing tape was used to couple the ultrasound into the material, which also protected the sample from damage due to the sonotrode.

The principle of the technique is to utilise two ultrasonic probes operating at different frequencies, modulated $\rho/2$ out of phase, and to operate the thermal camera 17 at twice this modulation frequency to perform the lock-in sampling routine. The component resonance should, therefore, be minimised so that internal heating of the actual BVID site can be observed more clearly.

Each sonotrode requires its own dedicated amplifier and machined head. The two sonotrodes operating at 35 kHz and 40 kHz were, therefore selected because they are still in the range for high power ultrasonic energy and were easily available off the shelf without the need to develop a bespoke ultrasonic amplifier at great expense.

There follows a review of literature relating to the propagation of ultrasound in thin plates and the absorption of ultrasonic waves in solids. This review will facilitate a greater understanding of how ultrasonic energy propagates within the material for the J-nose.

Figure 3A:
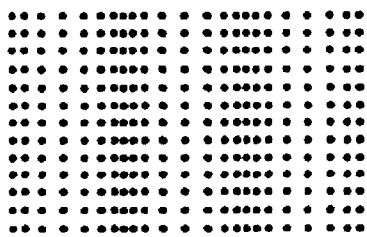
FIG. 3 shows, diagramatically, longitudinal (a) and shear (b) waves in an infinite solid.
Figure 3B:
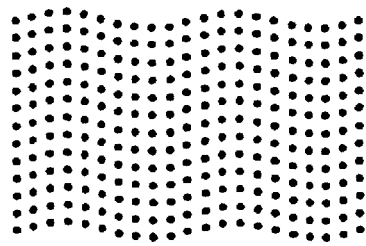

Inputting ultrasound on an infinite solid subjects particles of the medium to a small displacement from their equilibrium position. Elastic forces exerted by other particles in the medium tend to return the initial displacements back to the equilibrium position. Longitudinal and shear waves can, therefore, propagate in an infinite solid as illustrated in (a) and (b) respectively in FIG. 3 and can exist independently in the same sample.

Figure 4A:
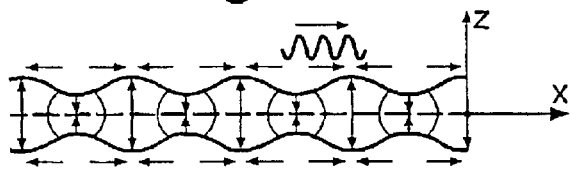
FIG. 4 is a schematic representation of vibrational motion of (a) symmetric and (b) anti-symmetric Lamb waves and (c) transverse waves-in plates.
Figure 4B:
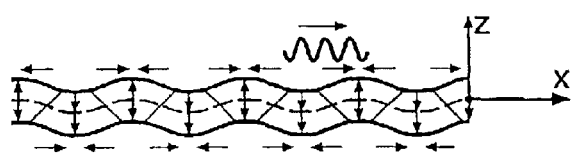
Figure 4C:
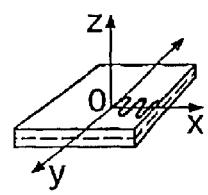

Elastic waves can also exist in finite-sized solids and are known as normal waves, which are determined by the local shape elasticity of the component. Normal waves can be classified as either Lamb waves or transverse waves and for a finite sized plate Lamb waves can exist as either (a) symmetrical or (b) anti-symmetrical, which are illustrated schematically in FIG. 4.

In a plate of thickness 2d at a frequency ω there can exist a finite number of symmetrical and anti-symmetrical Lamb waves, differing from one another by their phase and group velocities and distribution of the displacements and stresses throughout the thickness of the plate. Lamb waves can be excited by creating perturbations on the surface of a plate, inside a plate or at the end face of a plate, which results in the propagation of a travelling wave.

Only two zero-order Lamb waves, longitudinal $s_0$ and bending $a_0$, can exist in a thin plate defined by:
Where
ω=Angular frequency (rad.s$^{-1}$)
h=Plate thickness (m)
$c_t$=Transverse sound velocity (m.s$^{-1}$)

For the J-nose material $c_t$ was measured to be approximately 2800 m.s$^{-1}$ and h is approximately 1.1 mm. The two sonotrode frequencies operating at 35 kHz and 40 kHz are well below the upper boundary of approximately 400 kHz for the propagation of Lamb waves. Lamb waves should, therefore, propagate within the J-nose material.

Propagation of ultrasonic waves in real media is accompanied by attenuation dependent on geometric factors, scattering and energy dissipation. Attenuation due to divergence results in an intensity drop proportional to the square of the distance from the sound source. In an infinite medium Lamb waves continue to propagate but in finite media standing waves can be set up due to reflection from boundaries. In real components boundaries take the form of component edges or internal structure generating reflections which cause standing waves. Although the J-nose is a larger component than small coupons previously investigated one might, therefore, also expect to see standing waves generated within the J-nose component due to the stiffeners and material edges.

A series of trial experiments were conducted in order to understand the propagation of the high intensity ultrasonic energy within the J-nose component. FIG. 6 demonstrates heating between the stiffeners and the location of the BVID. The trial experiments demonstrated that the high energy ultrasound can only be coupled into the component if the sonotrode head is placed in the manner illustrated in FIG. 5 with the edge of the stiffener located on the central line of the sonotrode head.

Figure 5:
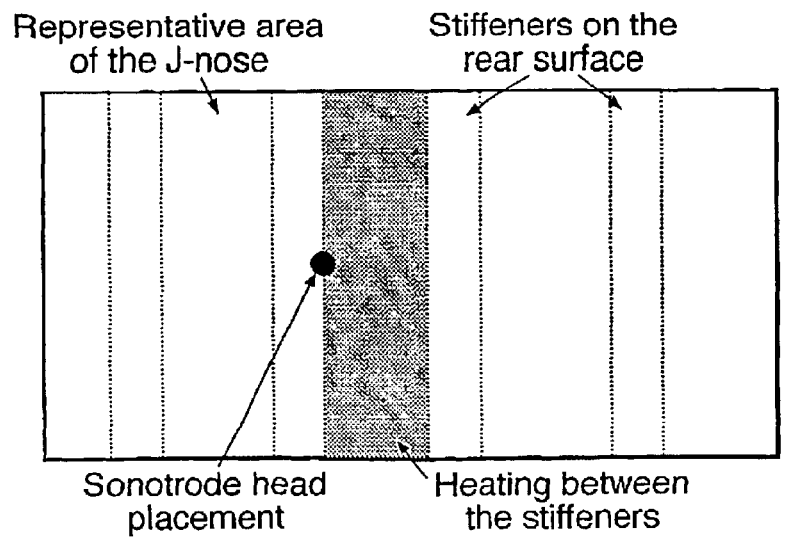
FIG. 5 shows placement of a sonotrode head to couple the ultrasonic energy.
Figure 6:
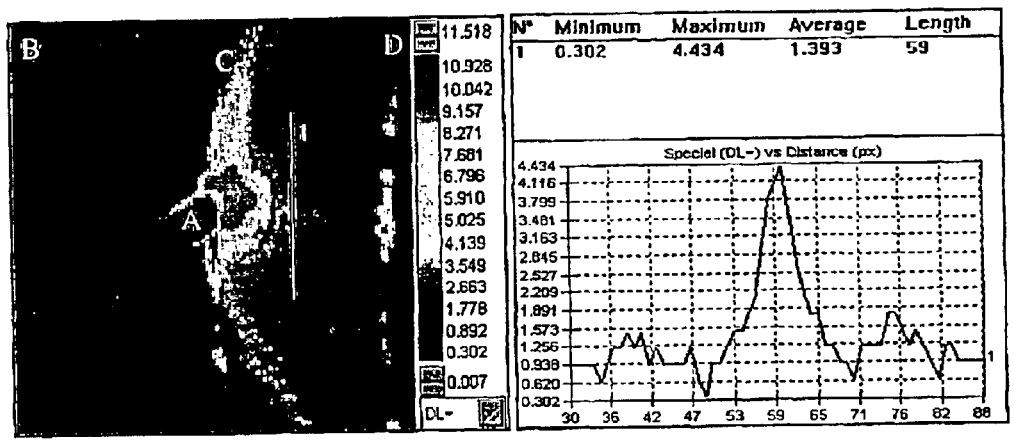
FIG. 6 shows a lock-in amplitude thermal image for 0.05 Hz modulation frequency.

FIG. 5 illustrates that the entire area between the stiffeners heats up only if the sonotrode is placed at a very precise location. Standing Lamb waves can also be seen in the thermal image producing areas of increased heating in addition to the broad area heating between the stiffeners.

Prior to the completion of well defined experimental investigations to determine the optimum sampling parameters for the thermal camera a number of trial experiments were conducted to consider the optimum loading parameters and location for the ultrasonic transducers. An investigation was completed into the likely position in which a transducer should-be placed on the J-nose to determine the best location to couple the ultrasound into the component. The thermal image contained in FIG. 6 was captured for a modulation frequency of 0.05 Hz with a sampling time of 12 seconds and a total image number of 250.

The large area illustrated within the thermal image in FIG. 6 is approximately 40 cm by 40 cm and shows the 40 kHz sonotrode A and three stiffeners on the rear surface of the component located at positions B, C and D. The BVID site can be observed in the thermal image set up between the sonotrode head and stiffener D and between the sonotrode head and the curvature of the wing skin at the bottom of the image to produce areas of increased heating.

The trial experiments demonstrated that there are specific locations where the ultrasound can be effectively coupled into the material. These locations are where the edge of a stiffener, located on the rear surface, is directly underneath the central point of the sonotrode head with the configuration illustrated in FIG. 5. In thermal images where the ultrasonic energy was absorbed into the component the area between stiffeners C and D heated up significantly whereas the area between stiffeners B and C did not heat up at all. The location of all three stiffeners can also be observed as the bond lines heat up due to the absorption of more of the ultrasonic energy than the component surface. An additional area of heating can be observed on the mid-point of stiffener D in line with the BVID site and the position of the sonotrode head. This point acts as a node for the reflected Lamb wave between the stiffeners and, therefore, acts as an energy absorber producing heat.

Figure 7:
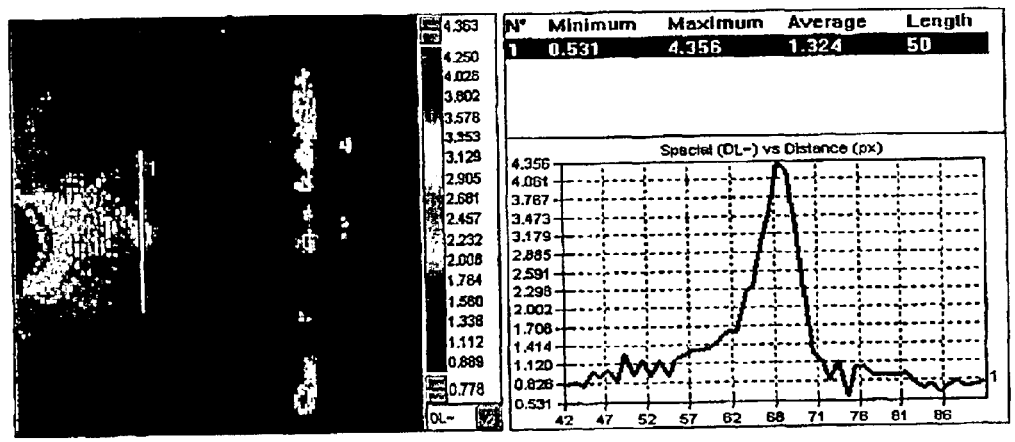
FIG. 7 shows a 40 kHz amplitude image for 0.15 Hz modulation frequency.

For the 40 kHz transducer a clear image illustrating the BVID with the smallest noise to signal ratio was produced for the 0.15 Hz modulation frequency and is presented in FIG. 7 together with the line profile plot.

FIG. 7 illustrates that the BVID is clearly visible in the area between the stiffeners. Areas of increased heating can be observed due to standing Lamb waves set up between the sonotrode head and areas of the J-nose component due to local area shape elasticity. The stiffener located on the right side of the thermal image heats up because it is effectively a node for the travelling and standing waves propagating from the sonotrode head and, therefore, a fixed point that absorbs energy.

Figure 8:
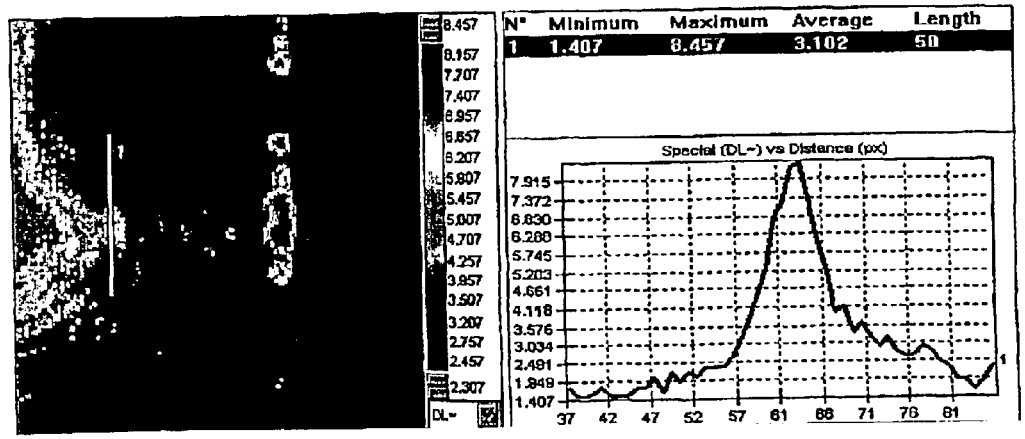
FIG. 8 shows a 35 kHz amplitude image for 0.05 Hz modulation frequency.

For the 35 kHz transducer a clear image illustrating the BVID with the smallest noise to signal ratio was produced for the 0.05 Hz modulation frequency and is presented in FIG. 8 together with the line profile plot.

The 35 kHz sonotrode used alone was not as effective in detecting the BVID site as the 40 kHz sonotrode. Although the BVID site is illustrated in the thermal image and in the line profile plot it is very unlikely to be detected without prior knowledge of its existence due to the other areas of anomalous heating. Standing Lamb waves are set up between the sonotrode head and BVID site and between the sonotrode head and stiffener located in the right of the thermal image. An additional standing wave can be seen directly below and to the right of the sonotrode head, which was set up between the curvature of the wing section and the sonotrode head. An area of Lamb wave superposition can also be observed to the right of the BVID site causing constructive interference, which results in triangular arrangement of hot spots.

For vertically oriented 35 kHz & 40 kHz transducers a clear image illustrating the BVID with the smallest noise to signal ratio was produced for the 0.15 Hz modulation frequency and is presented in FIG. 9 together with the line profile plot.

FIG. 9 illustrates that the BVID site is clearly visible between the stiffeners using the vertically mounted sonotrodes modulated in phase. Increased heating of the component can be observed between the sonotrodes and on the stiffener in the right of the thermal image. Standing waves were set up between the sonotrode heads but not between each sonotrode head and the stiffener in the right of the thermal image. The stiffener is also seen to heat up due to the reflection of the travelling Lamb wave.

For vertically oriented 35 kHz and 40 kHz transducers modulated out of phase a clear image illustrating the BVID with the smallest noise to signal ratio was produced for the 0.05 Hz modulation frequency and is presented in FIG. 10 together with the line profile plot.

FIG. 10 illustrates that the BVID site is clearly visible between the stiffeners using the vertically mounted sonotrodes modulated out of phase. Areas of increased heating due to standing waves can again be observed between the sonotrode heads and on the stiffener to the right of the thermal image due to travelling Lamb waves.

For horizontally oriented 35 kHz & 40 kHz transducers in phase a clear image illustrating the BVID with the smallest noise to signal ratio was produced for the 0.15 Hz modulation frequency and is presented in FIG. 11 together with the line profile plot.

FIG. 11 illustrates that the BVID site is clearly visible between the sonotrode heads mounted horizontally and modulated in phase. A standing Lamb wave was set up between the sonotrode heads and in general the technique reduced the level of anomalous heating regions.

For horizontally oriented 35 kHz and 40 kHz transducers out of phase a clear image illustrating the BVID with the smallest noise to signal ratio was produced for the 0.15 Hz modulation frequency and is presented in FIG. 12 together with the line profile plot.

The thermal image in FIG. 12 illustrates that the BVID site is clearly detectable for the horizontally oriented sonotrodes modulated out of phase. Areas of increased heating can be observed in a line between the sonotrode heads due to the standing Lamb wave. In general, however, areas of anomalous heating away from the sonotrode heads were reduced.

The methodology adopted in assessing the statistical relevance of the data collected was to complete 5 repetitions of two experimental trails using one modulation frequency for the vertically oriented sonotrodes in phase and out of phase. The raw data for these repetitions is contained in Tables 1 and 2 for the in phase and out of phase vertically oriented sonotrode results respectively.

TABLE 1

| Repeated Trial | Maximum Signal | Average Signal | Signal:Noise Ratio |
|---|---|---|---|
| 1 | 6.654 | 2.309 | 0.302 |
| 2 | 8.814 | 2.204 | 0.250 |
| 3 | 9.255 | 2.672 | 0.289 |
| 4 | 8.119 | 2.366 | 0.291 |
| 5 | 10.082 | 2.545 | 0.252 |

TABLE 2

| Repeated Trial | Maximum Signal | Average Signal | Signal:Noise Ratio |
|---|---|---|---|
| 1 | 9.574 | 2.144 | 0.224 |
| 2 | 14.229 | 3.549 | 0.249 |
| 3 | 7.470 | 2.927 | 0.278 |
| 4 | 8.819 | 2.079 | 0.236 |
| 5 | 6.478 | 1.415 | 0.218 |

Calculating the standard deviation for the in phase and out of phase noise to signal ratio gives 0.021 in both instances. The results for the graphical comparison below are, therefore, presented with error bars of ±0.021 for all configurations of the sonotrode placement.

In order to effectively compare the lock in ultrasonic transducer results the noise to signal ratio for the BVID site relative to the background level within the drawn box in each thermal image was calculated for experimental trials 3a–f and plotted against modulation frequency. The results are presented graphically in FIG. 13.

FIG. 13 illustrates that a smaller noise to signal ratio represents a BVID site which is more easily detectable with a greater false call rate. The BVID site was detectable between the stiffeners for all sonotrode head placement configurations apart from experimental trial 3b using the 35 kHz sonotrode when used alone for modulation frequencies higher than 0.05 Hz. The graphs illustrate that the peak noise to signal ratio for each data series changed significantly for each configuration of the sonotrodes which was due to the very complex interaction of standing and travelling waves within the component. The data series for the in phase vertical and horizontal sonotrode orientations 3c and 3e are both statistically lower than the data series for the out of phase vertical and horizontal orientations 3d and 3f. This result illustrates that there is a clear improvement for BVID detection using two sonotrodes operating at different frequencies and modulated $\rho/2$ out of phase whilst sampling the thermal camera at twice the modulation frequency. This result verifies the patent claims made regarding the technique.

The lowest noise to signal ratio was produced for the horizontally oriented sonotrodes modulated $\rho/2$ out of phase whilst sampling the thermal camera at twice the modulation frequency. This result is summarised in the data series 3f in FIG. 13 which is the lowest data series on the graph. Although a range of modulation frequencies were investigated, in practice only one modulation frequency would be required to fully interrogate a component since there are no 'blind spots' using amplitude images. Phase images were less reliable at locating BVID and should only be used to reinforce conclusions drawn from the amplitude images.

The lock-in ultrasonic TNDT technique was demonstrated to be able to locate the 7j BVID with an acceptable false call rate. Thermal images illustrating the 7j site with the greatest clarity were obtained using 2 sonotrodes operating at different frequencies, modulated out of phase and sampled at twice the modulation frequency. A range of modulation frequencies were investigated and it was demonstrated that there were no 'blind spots' for amplitude images when using the two sonotrode techniques. In practice, therefore, only one modulation frequency would be required to detect defects. Phase images illustrate the BVID sites occasionally but are in general less reliable and should only be used to reinforce conclusions drawn from the amplitude images.

It requires accurate placement of the sonotrode heads to obtain thermal images illustrating the BVID site. However, with further development the technique could be applied to the in-service environment effectively. A system could be developed locating a number of sonotrodes within a hand held device to effectively use the technique in-service.

When comparing the results obtained from the small coupons in the inventor's co-pending patent application more uniform heating can be observed on the J-nose due to less spurious reflections from standing Lamb waves producing anomalous hot spots due to the superposition of waves. Input ultrasonic energy was demonstrated to propagate in the entire area between the stiffeners with the 7j BVID site visible at a maximum distance of 6 cm from a sonotrode head. The use of two sonotrodes was demonstrated to produce images with a smaller noise to signal ratio of the BVID site leading to the conclusion that increasing the number of sonotrode heads into an array could increase defect detection over a wider area.

The increased heating of the BVID site is caused by the ultrasonic carrier frequencies 35 kHz and 40 kHz and not due to the modulation frequency. Both frequencies were demonstrated to excite the damage to a similar level but in general the 35 kHz sonotrode produced more spurious heating of the component than the 40 kHz sonotrode. Component resonance due to Lamb waves cannot be removed using ultrasonic energies and it was demonstrated that the strongest Lamb wave was produced in the thermal image with the most visible defect illustrated in FIG. 12. This result indicates that Lamb waves are a necessary part of defect detection using ultrasonic energies.

What is claimed is:

1. An apparatus for detecting anomolies in a material sample, said apparatus comprising:
   at least two ultrasonic probes for delivering acoustic energy at different frequencies into said material sample;
   an amplitude modulated power supply for driving said at least two ultrasonic probes; and
   an infrared camera for imaging at least a portion of said material sample affected by said acoustic energy and indicating said anomalies in said sample.

2. The apparatus of claim 1, wherein said power supply modulates power applied to each of said ultrasonic probes with a sinusoidal signal.

3. The apparatus of claim 2, wherein said the sinusoidal signal applied to one of said at least two ultrasonic probes is out of phase with the sinusoidal signal applied to the other of said at least two probes.

4. The apparatus of claim 3, wherein the sinusoidal signal applied to one probe is $\pi/2$ out of phase with the signal applied to the other probe.

5. The apparatus of claim 1, wherein said infrared camera samples said image of at least a portion of the material sample at a non-zero multiple of the modulation frequency of said ultrasonic probes by said power supply.

6. The apparatus of claim 5, wherein said infrared camera samples said image of at least a portion of the material sample at twice the modulation frequency of said ultrasonic probes by said power supply.

7. The apparatus of claim 1, wherein said probes operate at an ultrasonic frequency of in the frequency range of 10 kHz to 1 MHz.

8. The apparatus of claim 7, wherein one of said probes operates at an ultrasonic frequency of substantially 35 kHz and the other of said probes operates at an ultrasonic frequency of substantially 40 kHz.

9. An apparatus for detecting anomolies in a material sample, said apparatus comprising:

at least two ultrasonic probes for delivering acoustic energy at different frequencies into said material sample;

amplitude modulated power supply for driving said at least two ultrasonic probes at a modulation frequency, wherein said modulation is sinusoidal; and an infrared camera for imaging at least a portion of said material sample affected by said acoustic energy, said camera sampling at a frequency which is twice the modulation frequency, said camera indicating said anomalies in said sample.

10. The apparatus of claim 9, wherein the sinusoidal signal applied to one probe is $\pi/2$ out of phase with the signal applied to the other probe.

11. The apparatus of claim 9, wherein said imaging step includes imaging said portion of the material sample at a frequency that is a non-zero multiple of the modulation frequency of said ultrasonic probes by said power supply.

12. The apparatus of claim 11, wherein said imaging occurs at twice the modulation frequency of said ultrasonic probes by said power supply.

13. The apparatus of claim 9, wherein one of said probes operates at an ultrasonic frequency of substantially 35 kHz and the other of said probes operates at an ultrasonic frequency of substantially 40 kHz.

14. A method of detecting anomolies in a material sample, said method comprising the steps of:

delivering acoustic energy from at least two ultrasonic probes at different frequencies into said material sample;

amplitude modulating the acoustic energy from said at least two ultrasonic probes; and imaging by means of an infrared camera at least a portion of said material sample affected by said acoustic energy and indicating said anomalies in said sample.

15. The method of claim 14, wherein said amplitude modulation is by a sinusoidal signal.

16. The method of claim 15, wherein the sinusoidal signal applied to one of said at least two ultrasonic probes is out of phase with the sinusoidal signal applied to the other of said at least two probes.

17. The method of claim 14, wherein said probes operate at an ultrasonic frequency of in the frequency range of 10) kHz to 1 MHz.

* * * * *